United States Patent [19]
Bertho et al.

[11] Patent Number: 6,087,403
[45] Date of Patent: Jul. 11, 2000

[54] EMULSIFYING COMPOSITION BASED ON POLYGLYCOSIDES AND FATTY ALCOHOL

[75] Inventors: Jean-Noel Bertho, Pomacle; Philippe Mathaly, Reims; Regis de Baynast, Versailles; Veronique Dubois, Reims, all of France

[73] Assignee: Agro Industrie Recherches et Developments (A.R.D.), Pomacle, France

[21] Appl. No.: 09/131,014

[22] Filed: Aug. 7, 1998

[30] Foreign Application Priority Data

Aug. 8, 1997 [FR] France ................................. 97 10213

[51] Int. Cl.[7] .............................. B01F 17/56; A61K 7/02; A61K 7/42; C11D 3/22

[52] U.S. Cl. ........................ 516/72; 424/59; 424/70.19; 424/70.31; 510/417; 514/846; 514/847; 514/938; 516/925; 516/928

[58] Field of Search ............................ 516/72; 510/417; 514/938, 846, 847; 424/70.19, 70.31

[56] References Cited

U.S. PATENT DOCUMENTS

| | | | |
|---|---|---|---|
| 5,017,305 | 5/1991 | Hoeffkes et al. ........................ | 516/72 X |
| 5,268,126 | 12/1993 | Balzer ........................................ | 516/72 |
| 5,605,651 | 2/1997 | Balzer .................................... | 516/72 X |
| 5,670,471 | 9/1997 | Amalric et al. ...................... | 510/417 X |
| 5,741,766 | 4/1998 | Marion et al. ....................... | 510/417 X |
| 5,750,513 | 5/1998 | Hoorne et al. ......................... | 516/72 X |
| 5,830,483 | 11/1998 | Seidel et al. ......................... | 510/417 X |
| 5,888,482 | 3/1999 | Amalric et al. ...................... | 514/938 X |

FOREIGN PATENT DOCUMENTS

| | | |
|---|---|---|
| 92/06778 | 4/1992 | WIPO . |
| 95/13863 | 5/1995 | WIPO . |
| 96/37285 | 11/1996 | WIPO . |

*Primary Examiner*—Richard D. Lovering
*Attorney, Agent, or Firm*—Knobbe, Martens, Olson & Bear, LLP

[57] ABSTRACT

This composition based on polyglycosides comprises 30 to 65% by weight of at least one fatty alcohol of formula ROH, where R is a staturated or unsaturated, straight-chained or branched aliphatic radical having 1 to 4 ethylenically unsaturated bonds and having 12 to 22 carbon atoms, the remainder being a mixture of polyglycosides containing 35 to 75% by weight, based on the polyglycosides, of polyhexosides.

15 Claims, No Drawings

EMULSIFYING COMPOSITION BASED ON POLYGLYCOSIDES AND FATTY ALCOHOL

The present invention relates to a composition comprising a mixture of polyglycosides and at least one fatty alcohol, the use of these compositions as emulsifying compositions, self-emulsifiable compositions for the preparation of emulsions and emulsions containing such a composition.

Emulsions are widely produced and used in industry as substances for consumption, or for application to surfaces as carriers of agents which are insoluble in water. Emulsions are found in cosmetics (lotions, creams, ointments), in cooking (sauces, creams), in pharmaceuticals (ointments, creams), in painting (low-odour paint), in the road industry (emulsified bitumen), in agrochemicals (plant protecting agents), in detergents, in rolling, iron and steel production and in the manufacture of various deposits or coatings (printing, adhesives, etc.).

In cosmetics and pharmaceuticals, for the production of hygiene or beauty products, emulsions constitute an effective means of achieving a harmonious combination of ingredients of different types and properties in a uniform presentation which is easy to use. The emulsifiers most commonly used hitherto are alkylsulphates and sulphonates, alcohols, acids, ethoxylated fatty esters, fatty esters of sorbitan, etc.

Numerous plant protection compounds are water-insoluble and, having previously been solubilised in an organic solvent, they can be emulsified in water at the time of application or formulation by a suitable choice of emulsifiers.

The majority of emulsifiers are found in liquid forms of plant protection agents. The emulsifiable concentrate which is the most common form and still most frequently used on the market today conventionally contains 250 g/l of pesticides, for example, and 50 g/l of emulsifiers. The product is used by forming a fine emulsion the stability of which has to be ensured for a number of hours irrespective of temperature or water hardness. Concentrated suspensions are a more recent development and correspond to the production of formulations which enable very low doses to be administered per hectare. This is the case, for example, with concentrated emulsions which contain, respectively, 400 to 600 g/l of pesticides and 50 to 100 g/l of emulsifiers. Unlike the two forms described above, microemulsions are thermodynamically stable systems which are therefore of great interest from the point of view of storage of the products.

The emulsifiers used in the plant protection field are essentially, in terms of anionics, calcium dodecyl benzenesulphonate, amine alkylarylsulphonates, ethoxylated phosphate esters of fatty alcohol or ethoxylated alkylphenols. In terms of non-ionics, the most frequently used are the ethoxylated alkylphenols, the alcohols and ethoxylated fatty acids.

The preparation of emulsions using non-ionic polyoxyethylenated surfactants is well known.

These emulsifying surfactants may take the form of compositions based on fatty alcohols, acids or fatty esters which have the advantage of being "self-emulsifying". The term "self-emulsifying" denotes a composition which can produce a stable emulsion simply by mixing with an aqueous phase by gentle shaking.

The polyoxyethylenated non-ionic surfactants mentioned above have the disadvantage, for applications in cosmetics, dermatology and pharmaceuticals, in particular, of being irritant in some cases and being liable to contain undesirable impurities linked with the use of ethylene oxide, such as 1,4-dioxane, for example.

Moreover, it has been found that the emulsions prepared with these self-emulsifying compositions were stable only over a relatively short period of time.

With the aim of overcoming these drawbacks, the Application WO-92/06778 proposed the use of self-emulsifying compositions based on fatty alcohols and alkyl polyglycosides or polyosides. The latter preferably contain a mixture of alkyl polyglycosides in which the fatty chains have 16 and 18 carbon atoms, as well as a mixture of fatty alcohols with the same length of fatty chain.

However, it has been found on the one hand that the use of the self-emulsifying composition according to WO-92/06778 did not always produce sufficiently stable emulsions, especially with concentrations of compositions of less than 5% by weight based on the total weight of the emulsion.

On another hand, it was found in EP Application 0628305 that the use of the self-emulsifying composition according to WO 92/06778 did not allow the production of emulsions which showed sufficient stability over time in the presence of vegetable oils which are particularly rich in linoleic acid, such as sunflower oil, wheatgerm oil, soya oil and grapeseed oil, etc.

However, this linoleic acid has a very important part to play in maintaining the lipid structures of the intercellular spaces in the stratum corneum and in the restoration of the barrier function in dry skins.

The applicants also found that silicon oils are also difficult to put into stable emulsions. However, these oils are useful because they produce emulsions with a pleasant touch, having good penetration and generally water-resistant.

The present invention therefore proposes the preparation of compositions based on polyglycosides and fatty alcohols which can be used to produce stable emulsions (i.e. those which show no phase separation after three months of ageing at 45° C.) even using less than 5% by weight of composition based on polyglycosides according to the invention compared with the total weight of the emulsion, even in the presence of vegetable oils rich in linoleic acid or silicon oils.

The good stability of the emulsions has been achieved by the use of compositions according to the invention containing polypentosides, selected from among the polyarabinosides and the polyxylosides, in well defined proportions.

Furthermore, the applicants have found that the stability of the emulsions prepared from the composition according to the invention showed little sensitivity to the presence of salts. This means, in particular, that emulsions can be prepared containing ingredients charged with salts which hitherto it has sometimes been difficult to put into stable emulsions.

Moreover, the emulsifying compositions according to the invention consisting of polyglycosides and fatty alcohols, do not have the drawbacks of the compositions based on polyoxyethylenated compounds mentioned hereinbefore. They are not irritant, they are not toxic and they are biodegradable. In addition, the emulsifying compositions according to the invention may be used as self-emulsifying compositions.

The present invention therefore relates to an emulsifying composition based on polyglycosides, characterised in that it contains 30 to 65% by weight of at least one fatty alcohol of formula ROH, where R is a straight-chained or branched aliphatic radical which is saturated or unsaturated having 0 to 4 ethylenically unsaturated bonds and having 12 to 22 carbon atoms, the remainder consisting, apart from impurities, of:

(a) a mixture of polyglycosides containing 35 to 75% by weight, of at least one polyglycoside of formula:

$$R^1O(H_x)_{n1}$$

wherein $R^1$ is a straight-chained or branched aliphatic radical which is saturated or unsaturated having 0 to 4 ethylenically unsaturated bonds and with 12 to 22 carbon atoms, $H_x$ is the radical of a hexose, n1 is between 1 and 5; and 25 to 65% by weight of at least one polypentoside of formula:

$$R^2O(P_n)_{n2}$$

wherein $R^2$ is a saturated or unsaturated, straight-chained or branched aliphatic radical having 0 to 4 ethylenically unsaturated bonds, and having 12 to 22 carbon atoms, $P_n$ is the radical of a pentose selected from arabinose and xylose, n2 is between 1 and 5;
(b) or a mixture of polyglycosides of formula:

$$R^3O(G_1)_a(G_2)_b(G_3)_c(G_4)_d(G_5)_e$$

wherein $R^3$ is a straight-chained or branched aliphatic radical which is saturated or unsaturated having 0 to 4 ethylenically unsaturated bonds and having 12 to 22 carbon atoms, $G_1$, $G_2$, $G_3$, $G_4$ and $G_5$ independently of one another are residues of an ose selected from the hexoses and pentoses, the latter being selected from arabinose and xylose, the hexoses representing 35 to 75% by weight of all the residues of oses $G_1$, $G_2$, $G_3$, $G_4$ and $G_5$ and the pentoses representing 25 to 75% by weight of all the residues of oses $G_1$, $G_2$, $G_3$, $G_4$ and $G_5$; a, b, c, d and e being equal to 0 or 1, and the sum of a, b, c, d and e being at least 1; or (c) a mixture of (a) and (b).

Each ose residue may be in the isomer form α or β, in the form L or D and in the form of a furanose or pyranose. Hexoses of series D, notably D-glucose, D-galactose and D-mannose, are preferred. Of the pentoses, L-arabinose and D-xylose which are present in large amounts in the hemicelluloses of numerous plants are preferred.

Owing to the abundance of glucose on the sugar market, glucosides preferably make up at least 80% of the hexosides.

The fatty alcohols of formula ROH having 14 to 22 carbon atoms and particularly the mixtures of hexadecanol and octadecanol are particularly preferred.

Moreover, on account of their speed of manufacture, the compositions according to the invention which contain polyglycosides wherein the $R^1$ and $R^2$ radicals or the $R^3$ radical are identical to the radical R of the fatty alcohol are most particularly preferred.

The present invention relates primarily to an emulsifying composition based on fatty alcohols and polyglycosides. Because of their effectiveness and ease of production, compositions containing 40 to 60% by weight of fatty alcohols based on the total weight of the composition and preferably 52 to 57% of fatty alcohol, the remainder consisting of polyglycosides, apart from any impurities, are most particularly preferred.

The compositions based on polyglycosides and fatty alcohols according to the invention can be prepared simply by mixing their components in the proportions as specified hereinbefore. The homogenisation techniques used are those currently used for mixing solid or liquid ingredients. For the solid ingredients, however, it is preferable if at all possible to mix them at a temperature above their melting points in liquid form.

However, on an industrial scale, the compositions according to the invention are prepared by one of the two methods conventionally used for synthesising alkyl polyglycosides.

The first method consists in contacting the reducing sugar and the fatty alcohol directly in the presence of an acid catalyst in order to obtain the polyglycosides.

The second method consists of carrying out glycosidation, in a first step, with a short alcohol corresponding to formula $R^4OH$, where $R^4$ is a $C_{1-5}$-alkyl radical. In a second step, transglycosidation is carried out, which consists of displacing the short alcohol of formula $R^4OH$ with a fatty alcohol.

Each of these two methods may, as appropriate, be supplemented by operations of neutralisation, filtration, elimination of excess fatty alcohol and decolorisation.

Advantageously, particularly if crystallised reducing sugars are used as starting materials, it is preferable to use the first direct method which has the advantage of being quicker and easier to carry out. However, when reducing sugars are used in the form of syrups, it is preferable to use the second method which produces a more homogeneous reaction medium and consequently higher quality polyglycosides which contain no or very few breakdown products.

The term reducing sugars refers to the hexoses, pentoses and corresponding oligosaccharides which have a free anomeric hydroxyl.

In the direct glycosidation of sugars with fatty alcohol or a mixture of fatty alcohols or during transglycosidation if the grafting is carried out in two steps, the fatty alcohol is preferably used in excess (1 to 3 and preferably 1.5 to 2 molar equivalents based on the reducing sugars), so that the reaction product contains the quantities specified above of free fatty alcohol and polyglycosides.

It is also possible for the fatty alcohol or mixtures of fatty alcohols to be eliminated partly or totally at the end of the synthesis and then for a fatty alcohol or mixture of fatty alcohols different from or identical to those used in the synthesis to be added in specified proportions in order to obtain the composition according to the invention.

However, the first solution is preferred, which comprises using the fatty alcohol in an excess so that the reaction product contains the specified amounts of fatty alcohols and polyglycosicies.

In practice, there are three main ways of obtaining the compounds according to the invention from reducing sugars and fatty alcohols.

The first method consists in carrying out the glycosidation of the reducing sugars (hexoses such as glucose, galactose, mannose and the corresponding oligosaccharides, pentoses selected from arabinose and xylose and the corresponding oligosaccharides) separately by contacting with one or more fatty alcohols in the presence of an acid catalyst conventionally used for reactions of glycosylation. Preferably, the fatty alcohol is used in excess (1 to 3, preferably 1.5 to 2 molar equivalents based on the reducing sugars) so that the reaction product contains the specified amounts of free fatty alcohol and polyglycosides. After neutralisation of the acid catalyst, the polyhexosides of formula:

$$R^1O\,(H)_{n1}$$

and the polypentosides of formula:

$$R^2O(P)_{n2}$$

are obtained. Then, 35 to 75%, advantageously 45 to 70% and preferably 50 to 65% by weight, based on the total weight of the polyglycosides, polyhexosides and 25 to 65%, advantageously 30 to 55% and preferably 35 to 50% by weight of polypentosides, based on the total weight of polyglycosides, are added to the mixture, if necessary in the presence of fatty alcohol of formula ROH, to obtain the compositions according to the invention.

The second method consists in mixing 35 to 75%, advantageously 45 to 70% and preferably 50 to 65% by weight of hexoses and/or corresponding oligosaccharides, based on the total weight of reducing sugars, with 25 to 65%, advantageously 30 to 55% and preferably 35 to 50% by weight of pentoses and/or the corresponding oligosaccharides, based on the total weight of reducing sugars, and carrying out glycosidation of the mixture of reducing sugars thus obtained. The glycosylation is carried out in the presence of a an acid catalyst with an excess (1 to 3, preferably 1.5 to 2 molar equivalents based on the reducing sugars) of fatty alcohol in such a way that, preferably, the reaction product contains the specified amounts of free fatty alcohols. The composition is neutralised and if necessary the fatty alcohol of formula ROH is added in order to arrive at the amounts specified hereinbefore.

Finally, the third method consists of using syrups of mixtures of reducing sugars derived from raw plant materials rich in starch and hemicellulose, or products or by-products of agricultural origin such as products or by-products of maize (maize bran, fibres and pomace), barley (bran) or by-products of wheat as described in Patent Application EP 0 699 472 containing hexoses and pentoses, and carrying out glycosidation of these syrups of reducing sugars with fatty alcohols in order to obtain the compositions according to the invention.

By maize products is meant the entire plant and/or its constituent parts (cobs, shucks, stalks and leaves) which can be harvested directly or be obtained from the waste after separation of the grains.

It is also possible to use maize fibre or bran. By maize fibre is meant the compounds obtained during a process of fractionation which sets out notably to produce starch.

By maize pomace is meant the by-products obtained either by alcoholic fermentation or after the production of starch under wet conditions in a starch producing plant, which consist notably of mixtures of hemicellulose and starch.

According to one particular feature of the invention, this third way is preferred, which has the advantage of using syrups of reducing sugars (consisting of hexoses and pentoses) which are less expensive than the hexoses (glucose) and pentoses in the market and thereby obtaining cheap compositions based on polyglycosides.

It is particularly preferred to use syrups of reducing sugars obtained by hydrolysis of by-products of plant origin containing in particular starch and hemicellulose.

It is most particularly preferred to use syrups of reducing sugars derived from wheat, notably wheat bran, wheat fibres as defined in the application EP 0699 472, syrups of sugars derived from the by-products of maize (maize bran, maize pomace).

According to an advantageous feature which is linked particularly to the natural origin of the composition of the sugar syrups used for preparing the polyglycosides of the compositions according to the invention, it is particularly preferred to use compositions based on polyglycosides containing 45 to 70% by weight of polyhexosides based on the polyglycosides and 30 to 55% by weight of polypentosides and notably 50 to 65% by weight of polyhexosides and 45 to 50% by weight of polypentosides.

For this reason, in the light of the previous remarks and according to a particular feature of the invention, the compositions according to the invention are preferably obtained by contacting a syrup of reducing sugars derived from the plant raw material containing starch and hemicellulose in such a way that the polyglycosides of the compositions according to the invention contain the specified amounts of polyhexosides and polypentosides, with a short alcohol of formula $R^4OH$, in the presence of 0.1 to 5% by weight, based on the dry content of the sugars, of an acid catalyst such as sulphuric acid, hydrochloric acid, a sulphonic acid such as methanesulphonic acid, hypophosphorous acid or any other acid catalyst which will cause glycosidation and mixtures thereof, at a temperature of between 50 and 110° C.

Subsequently, transglycosidation is carried out, under reduced pressure (2 to 300 mb), at a temperature between 50 and 100° C., using a fatty alcohol or mixture of fatty alcohols of formula ROH used in excess (1 to 3, preferably 1.5 to 2 molar equivalents based on the reducing sugars), so that the reaction product contains the quantities of fatty alcohol and polyglycosides specified hereinbefore.

The acid catalyst is then neutralised. The neutralisation is carried out, for example, using a hydrogen carbonate or an alkali metal or alkaline earth metal carbonate, notably sodium hydrogen carbonate, an alkali metal or alkaline earth metal hydroxide, notably sodium hydroxide, or an organic base such as triethanolamine. If required, some or all of the free fatty alcohol can subsequently be evaporated off and the composition can be decolorised in the presence of hydrogen peroxide, for example.

At the end of the synthesis, depending on the fatty alcohol or mixture of fatty alcohols used, the composition will be in the form of a solid wax, paste or liquid. From a solid wax it is possible to obtain powder, flakes or even beads, for subsequent ease of use. It is preferable to isolate the composition in the form of a powder which is very easy to use thereafter, especially to produce emulsions.

According to another aspect of the invention, the polyglycoside-based compositions according to the invention may be used for preparing emulsions containing at least an aqueous phase and an oily phase, characterised in that they contain:

2 to 60% by weight of at least one oil 1 to 10% by weight of the composition based on alkyl glycosides of the emulsion optionally other emulsifying compositions such as polyoxyethylenated surfactants, mixtures of fatty alcohols and polyoxyethylenated and glycoside surfactants, waxes, etc. The remainder essentially consists of an aqueous phase.

The oily phase of the emulsion may consist of an oil selected from:

the vegetable oils such as sweet almond oil, coconut oil, castor oil, jojoba oil, olive oil, rapeseed oil, groundnut oil, hazelnut oil, palm oil, shea tree butter, apricot kernel oil, calophyllum oil, safflower oil, avocado oil, derivatives of these oils such as the hydrogenated oils, the plant oils rich in linoleic acid such as walnut oil, blackcurrant seed oil, wheatgerm oil, sunflower oil, maize germ oil, soya oil, cotton seed oil, alfalfa oil, barley oil, grapeseed oil, poppyseed oil, pumpkin seed oil, sesame oil, rye oil, evening primrose oil, saffron oil, passion flower oil, derivatives of these oils such as the hydrogenated oils, oils of animal origin (tallow, fish oils etc.), mineral oils such as paraffin oil, vaseline oil and the mineral oils obtained in particular from petroleum fractions, synthetic oils such as the poly-α-olefins, lanolin derivatives, diols such as 1,2-propanediol, 1,3-butanediol, alcohols such as cetyl alcohol, stearyl alcohol and oleic alcohol, polyethyleneglycols or polypropyleneglycols, fatty esters such as alkyl myristates, especially butyl myristate, propyl myristate, alkyl palmitates such as isopropyl palmitate, alkyl stearates, especially hexadecyl stearate, alkyl oleates, particularly dodecyl oleate, alkyl laurates, particularly hexyl laurate, propyleneglycol dicaprylate, ethyl-2-hexyl cocoate, esters of lactic acid, behennic acid and isostearic acid, such as isostearyl isostearate, the silicon oils combining the cyclic polydimethylsiloxanes, α-ω-hydroxylated polydimethylsiloxanes, α-ω-trimethylsilylated polydimethylsiloxanes, polyorganosiloxanes such as the polyalkylmethylsiloxanes, polymethylphenylsiloxanes, polydiphenylsiloxanes, amino derivatives of silicones, silicone waxes, copolyether silicones (such as the oil SILBIONE 70646® sold by the company RHONE-POULENC or DC 190® sold by DOW CORNING) or mixed derivatives of silicones such as the mixed copolymers of polyalkylmethylsiloxanes/copolyether silicones.

Of course, the emulsions prepared from the composition according to the invention may also contain one or more conventional lipophilic or hydrophilic cosmetic adjuvants, particularly those which are already commonly used in the manufacture and production of emulsions. Of the conventional cosmetic adjuvants which are likely to be contained in the aqueous phase and/or fatty phase of the emulsions, the following may be mentioned in particular:

ionic or non-ionic thickeners and gelatinisers such as cellulose derivatives (carboxymethylcellulose, hydroxyethylcellulose), guar derivatives (hydroxypropyl guar, carboxymethyl guar, carboxymethylhydroxypropyl guar), carob derivatives, tree exsudates (gum arabic, karaya), seaweed extracts (alginates, carrageenates), exsudates from microorganisms (xanthane gum), hydrotropic agents such as short $C_{2-8}$-alcohols, particularly ethanol, the diols and glycols such as diethyleneglycol and propyleneglycol, hydrating or moisturising agents for the skin such as glycerol, sorbitol, collagen, gelatine, aloe vera, hyaluronic acid, urea or skin protectors such as proteins or protein hydrolysates, cationic polymers such as cationic guar derivatives (JAGUAR C13S®, JAGUAR C162®, HICARE 1000® sold by RHONE-POULENC), glycolipids such as lipid sophoroses, mineral powders or particles such as calcium carbonate, mineral oxides in powder form or colloidal form (particles which are smaller than or of the order of 1 micron, sometimes several tens of nanometers) such as titanium dioxide, silica, aluminium salts generally used as antiperspirants, kaolin, talc, clays and derivatives thereof, preservatives such as methyl, ethyl, propyl and butyl esters of p-hydroxybenzoate acid, sodium benzoate, GERMABEN® or any chemical agent which prevents bacterial growth or mould and which is conventionally used in cosmetic compositions are generally added to these compositions in amounts of 0.01 to 3% by weight.

Instead of these chemical agents it is sometimes possible to use agents which modify the activity of water and greatly increase osmotic pressure, such as carbohydrates or the salts thereof.

organic sun filters which are effective against UV-A and UV-B in order to protect the skin or hair from the effects of sun and UV-radiation, such as the compounds which are authorised in European Directive No. 76/768/EEC, the annexes thereto and subsequent modifications to this Directive, photoprotective mineral monopigments such as titanium dioxide or cerium oxides in the form of powder or colloidal particles, softeners, antioxidants, self-tanning agents such as DHA, insect repellants, vitamins, perfumes, fillers, sequestering agents, dyes, buffers, abrasive agents such as ground apricot kernels, microbeads. . . .

According to a preferred use of the invention, the percentage by weight of the emulsifying composition based on polyglycosides constitute 2 to 6% by weight and preferably 3 to 4% of the total weight of the emulsion.

According to another preferred use of the composition according to the invention, the proportion of oil is between 10 and 40% by weight, based on the total weight of the emulsion.

Three main methods of producing the emulsions are proposed:

The first method comprises heating all the ingredients simultaneously to a temperature of between 50 and 90° C., then homogenising the mixture with a rotary paddle stirrer rotating at 500 to 15,000 rpm, particularly 1000 to 2000 rpm, at a temperature of between 50 and 90° C. and finally cooling the mixture, with gentle stirring (at 100 to 1000, particularly 300 to 500 rpm) to a temperature of the order of 25° C. If the homogenisation is intense when the mixture is hot, it is not always advisable to stir the emulsion as it cools.

The second method comprises operating by phase inversion. In this case, the lipophilic and hydrophilic phases are heated separately to a temperature of between 50 and 90° C. The lipophilic phase which contains the composition according to the invention is subjected to vigorous stirring with a rotary paddle stirrer rotating at 500 to 15,000 rpm, particularly 1000 to 2000 rpm, and the hydrophilic phase is slowly added to this phase, at a rate such that the hydrophilic phase is instantly absorbed by the lipophilic phase, until there is phase inversion characterised by an abrupt change in viscosity. The addition can then proceed more rapidly at a rate such that the hydrophilic phase stagnates above the lipophilic phase for 1 to 3 seconds if it is being added from above. The emulsion is then allowed to cool with gentle stirring (100 to 1000, particularly 300 to 500 rpm) down to a temperature of the order of 25° C.

The third method is carried out by dispersion. In this case the lipophilic phase and the hydrophilic phase (which contains the emulsifying composition according to the invention, are heated separately to a temperature of between 50 and 90° C. The hydrophilic phase is stirred with a rotary paddle stirrer rotating at 500 to 1500 rpm, particularly 1000 to 2000 rpm and the lipophilic phase is progressively added thereto at a rate such that the lipophilic phase is instantly absorbed by the hydrophilic phase. The emulsion is then left to cool with gentle stirring (from 100 to 1000, particularly 300 to 500 rpm) down to a temperature of the order of 25° C.

According to another aspect of the invention, the polyglycoside-based composition can be used as a self-emulsifying base for the preparation of emulsions by hot dispersion of the compositions of the invention, for example at between 50 and 90° C., in water or a suitable polar medium, simply by stirring, notably by mechanical stirring or sonication. If the composition is dispersed in water by stirring or sonication at a temperature close to the melting point of the emulsifying composition, dispersions rich in vesicles are obtained.

The emulsions prepared from the composition according to the invention may be used in various cosmetic or dermatological applications e.g. in the form of creams for the face, body, scalp or hair or in the form of a lotion for the body or for removing makeup or again in the form of ointments, e.g. for pharmaceutical use. These emulsions may also be used for makeup, notably in the form of foundations, after the addition of pigments. They can also be used as sun creams after the addition of UVA and/or UVB and/or DHA filters, or as after-sun creams or lotions after the addition of soothing compounds such as panthenol or shea tree butter.

The emulsions may also contain ionic or non-ionic surfactants with a washing, foaming or detergent effect, such as sodium laurylether sulphate, alkyl-betaines, APGs, etc., for producing washing emulsions such as moisturising washing creams or shaving emulsions.

The emulsions may also contain a cosmetic wax such as rice wax, candellila wax, Japanese wax, in order to improve their cosmetic qualities. The proportion of wax is generally between 0.5 and 3%, preferably between 1 and 2% by weight, based on the total weight of the emulsion.

The compositions based on polyglycosides and fatty alcohols according to the invention may also be used in formulations in which finely divided solids have to be kept suspended in water, such as formulations of agrochemical substances (herbicides, insecticides, fungicides) known under the generic name of "concentrated suspensions". Apart from a dispersant surfactant the additives found in a formulation of concentrated suspension are additives such as those described in the commercial brochure "Auxiliaries for agrochemical formulations" edited by RHONE-POULENC GERONAZZO SpA. Examples include a wetting surfactant chosen from the alkyl derivatives of aryl aliphatic alcohols, the aryl sulphonated derivatives such as sodium isopropyl-naphthalene sulphonate marketed under the name SUPRAGIL WP® by RHONE-POULENC GERONAZZO, the dialkylsulphosuccinates such as sodium di-ethyl-2-hexylsulphosuccinate, dispersant polymers such as polyacrylic acids and salts thereof, the maleic anhydride (or acid)/diisobutylene copolymers and salts thereof such as GEROPON T36® (RHONE-POULENC GERONAZZO), the condensed sodium methylnaphthalene sulphonates such as SUPRAGIL MNS90® (RHONE-POULENC GERONAZZO), the dispersant polymers derived from lignine such as sodium or calcium lignosulphonates or other dispersant surfactants such as the alkoxylated, optionally sulphated or phosphated derivatives of tristyryl phenols. These formulations may further contain anti-freeze additives such as propylene glycol and thickeners which modify the Theological behaviour of the suspension, such as xanthane gum, cellulose derivatives (carboxymethyl-cellulose), guar gum or derivatives thereof, clays or modified clays such as bentonite and bentones.

Among the active substances which may be formulated in this way are generally found those with a melting point above 45° C., preferably above 60° C., having a solubility in water of less than 10 g/l, preferably less than 1 g/l. The active plant protecting agents in question are herbicides, fungicides and insecticides such as those described in THE PESTICIDE MANUAL (9th edition, C. R. WORKLING and R. J. HANCE, editors, published by The British Crop Protection Council) and meeting the above criteria.

The following Examples set out to illustrate the present invention.

SYNTHESIS EXAMPLE 1
Process for preparing cetaryl polyglucosides 85.3 g of anhydrous D-glucose are suspended in 94.6 g of n-butanol in the presence of 1.7 g of sulphuric acid. The reaction medium is heated to the reflux temperature of the butanol until the reaction mixture becomes clear. This is then added, at 90° C., over 90 minutes and under reduced pressure (50 mb), to 225 g of fatty alcohol (70% hexadecanol, 30% octadecanol) containing 0.85 g of sulphuric acid and the butanol is eliminated under reduced pressure. The reaction mixture is kept under the same conditions for 30 minutes after all has been added. The acidity of the medium is neutralised with an aqueous sodium hydroxide solution, strength 30.5% (3.9 g) to give pH 7 to 8. The reaction product referred to as the composition based on cetaryl glucosides (310 g) is in the form of a solid paste containing 52% by weight of residual fatty alcohol. This is then brought to 55% based on the reaction product as a whole by the addition of 9.3 g of a mixture of hexadecanol and octadecanol (70/30) and then ground to obtain a powder with a particle size of less than 800 µm.

SYNTHESIS EXAMPLE 2
Process for preparing cetaryl polyxylosides 96.6 g of anhydrous D-xylose are suspended in 128.7 g of n-butanol in the presence of 1.93 g of sulphuric acid. The reaction mixture is heated to the reflux temperature of the butanol until the reaction mixture becomes clear. This is then added at 80° C., over 90 minutes and under reduced pressure (50 mb) to 306 g of fatty alcohol (70% hexadecanol, 30% octadecanol) containing 0.97 g of sulphuric acid and the butanol is eliminated under reduced pressure. The reaction medium is kept under the same conditions for 30 minutes after the addition has ended. The acidity of the medium is neutralised with an aqueous solution of sodium hydroxide, strength 30.5% (4.4 g) to pH 7 to 8. The reaction product referred to as the composition based on cetaryl xylosides (401 g) is in the form of a solid paste containing 46.5% by weight of residual fatty alcohol. This is then brought to 55%, relative to the reaction product as a whole, by the addition of 34 g of a mixture of hexadecanol and octadecanol (70/30) and is ground to obtain a powder with a particle size of less than 800 µm.

SYNTHESIS EXAMPLE 3
Process for preparing cetaryl polyarabinosides 90.7 g of anhydrous L-arabinose are suspended in 120.8 g of n-butanol in the presence of 1.81 g of sulphuric acid. The reaction medium is heated to the reflux temperature of the butanol until the reaction mixture becomes clear. This is then added at 80° C., over 90 minutes and under reduced pressure (50 mb), to 287.2 g of fatty alcohol (hexadecanol: 70%, octadecanol: 30%) containing 0.91 g of sulphuric acid and the butanol is eliminated under reduced pressure. The reaction medium is kept under the same conditions for 30 minutes after the addition has ended. The acidity of the medium is neutralised with an aqueous sodium hydroxide solution, strength 30.5% (4.2 g), to pH 7 to 8. The reaction product known as the composition based on cetaryl arabinosides (376 g) is in the form of a solid paste which contains 50.4% by weight of residual fatty alcohol. This is then brought to 55%, relative to the reaction product a,s a whole, by the addition of 17.3 g of a mixture of hexadecanol and octadecanol (70/30) and is ground in order to obtain a powder with a particle size of less than 800 µm.

EXAMPLE 1
Process for preparing a composition based on polyglycoside and cetaryl alcohol according to the invention 55 g of the composition based on cetaryl polyglucoside in synthesis Example 1, 30 g of the composition based on cetaryl polyxylosides in synthesis Example 2 and 15 g of the composition based on cetaryl polyarabinosides in synthesis Example 3 are mixed together to obtain 100 g of the composition based on polyglycosides characterised in that it comprises 55% by weight of fatty alcohol, the remainder being made up of cetaryl polyglycosides containing 55% by weight, based on the polyglycosides, of cetaryl polyhexosides and 45% by weight of cetaryl polypentosides (30% by weight of cetaryl polyxylosides and 15% by weight of cetaryl polyarabinosides).

EXAMPLE 2

Process for preparing a composition based on cetaryl polyglycoside and cetaryl alcohol according to the invention 3 g of 95% sulphuric acid are added to a suspension of a mixture of 65 g of anhydrous D-glucose, 5 g of D-galactose, 20 g of D-xylose and 10 g of L-arabinose in 284.5 g of a (50/50 weight/weight) mixture of hexadecanol/octadecanol. The reaction medium is heated to 90° C. under reduced pressure (30 mbar) for 2 hours 30 minutes. Then, at the same temperature, the acid catalyst is neutralised with 6.1 g of 30.5% aqueous sodium hydroxide and the product is decolorised in the presence of hydrogen peroxide and sodium hydroxide. After cooling to 20° C. and grinding the solid obtained, 380 g of the composition are obtained, which contains 54% by weight, based on the total weight of the composition of fatty alcohol.

EXAMPLE 3

Process for preparing a composition based on polyglycosides derived from wheat bran according to the invention A suspension of wheat bran containing 20% dry matter (100 kg of dry bran for 500 kg of suspension) is prepared in a sulphuric acid solution (10% $H_2SO_4$/bran DM). The reaction medium is homogenised in a stirred reactor then heated to a temperature of 130° C. for 30 minutes. After hydrolysis, the mixture is slaked to pH 5 with milk of lime and pressed on a filter press to separate the filter cakes from the liquor 1. This liquor 1 is then demineralised by ion exchange on a strong cationic resin (A 200), a weak anionic resin (A368S) and finally a strong cationic resin (A 200), successively. The liquor 2 obtained is then concentrated to 74.9% dry matter by evaporating the water under reduced pressure at 50° C. The composition of the syrup 3 obtained is given in the following Table:

|  | SYRUP 3 |
|---|---|
| Dry matter (%) | 74.9 |
| D-glucose/dry matter (%) | 33.8 |
| Other hexoses/dry matter (%) | 7.7 |
| D-xylose/dry matter (%) | 21.8 |
| L-arabinose/dry matter (%) | 16.6 |
| Oligosaccharides/dry matter (%) | 7.1 |
| Purity in reducing sugars/dry matter (%) | 87.0 |

350 g of this syrup 3 are then added dropwise over 1½ hours to 338.3 g of n-butanol containing 5.2 g of sulphuric acid and 22 g of water at a temperature of the order of 100 to 105° C. The water is eliminated in the course of the reaction by azeotropic distillation of the water/butanol mixture. The reaction mixture obtained is then added to 767.3 9 of fatty alcohol (hexadecanol: 30%, octadecanol: 70% by weight) containing 2.6 g of sulphuric acid, at a temperature of 90° C. over a period of 2 hours. The butanol is eliminated continuously under reduced pressure during the addition. Then, at the same time temperature, the acidity of the medium is neutralised with a 30.5% aqueous sodium hydroxide solution to pH 7 to 8 and the product is decolorised in the presence of oxygenated water. After cooling to 20° C. and grinding of the solid obtained, 1020 g of the composition are obtained, containing 57% by weight, based on the total weight of the fatty alcohol composition.

EXAMPLE 4

Process for preparing a composition based on polyglycosides derived from wheat bran according to the invention 100 g of the syrup 3 in Example 3 are added dropwise over 1½ hours to 96.7 g of n-butanol containing 1.5 g of sulphuric acid and 6.3 g of water at a temperature of the order of 100 to 105° C. The water is eliminated during the reaction by azeotropic distillation of the mixture of water and butanol. Then the reaction medium obtained is added to 165.3 g of fatty alcohol (dodecanol: 27%, tetradecanol: 23%, hexadecanol: 26%, octadecanol: 24% by weight) at a temperature of 90° C. over 2 hours. The butanol is eliminated continuously under reduced pressure during the addition. Then, at the same temperature, the acidity of the medium is neutralised with a 30.5% aqueous sodium hydroxide solution to pH 7 to 8. The fatty alcohols present in the reaction mixture are partly eliminated by distillation over a thin layer evaporator. A mixture is obtained containing 34% by weight of fatty alcohols as follows:

Dodecanol: 0.3 g

Tetradecanol: 2.6 g

Hexadecanol: 27.9 g

Octadecanol: 32.7 g 56.5 g of a mixture of hexadecanol/octadecanol (50/50, weight/weight) is added to the medium with a view to obtaining 243 g of the following composition containing:

0.1 weight % of free dodecanol 1.1 weight % of free tetradecanol 23.0 weight % of free hexadecanol 25.1 weight % of free octadecanol The remainder consists of polyglycosides, apart from any impurities.

EXAMPLE 5

Process for preparing a composition based on polyglycosides derived from wheat fibres according to the invention A suspension of wheat fibres (as defined in Patent Application EP 0 699 472) is prepared containing 20% dry matter (100 kg of dry fibrous material to 500 kg of suspension) in a sulphuric acid solution (10% $H_2SO_4$/DM of fibres). The reaction medium is homogenised in a stirred reactor, then brought to a temperature of 130° C. for 30 minutes. After the hydrolysis, the mixture is slaked to pH 5 with milk of lime and pressed in a filter press to separate the filter cake from the liquor 1. This liquor 1 is then demineralised by ion exchange on a strong cationic resin (A 200) and decolorised in the presence of 1% by weight, based on the total weight of liquor, of active charcoal (CG1 NORIT) for 30 minutes at 20° C. The charcoal is then eliminated by passing through a filter press then through a plate filter (cutoff threshold: 0.2 Am) to obtain a liquor 2. This liquor 2 is then concentrated to 74.1% dry matter by evaporating the water under reduced pressure at 50° C. The composition of the syrup 3 obtained is given in the following Table:

|  | SYRUP 3 |
|---|---|
| Dry matter (%) | 74.1 |
| D-glucose/dry matter (%) | 58.3 |
| Other hexoses/dry matter (%) | 1.6 |
| D-xylose/dry matter (%) | 14.6 |
| L-arabinose/dry matter (%) | 10.2 |
| Oligosaccharides/dry matter (%) | 6.5 |
| Purity of reducing sugars/dry matter (%) | 91.2 |

150 g of this syrup 3 are then added dropwise over 1½ hours to 138.7 g of n-butanol containing 1.3 g of sulphuric acid and 9 g of water at a temperature of the order of 100 to 105° C. The water is eliminated in the course of the reaction by azeotropic distillation of the water/butanol mixture. The reaction mixture obtained is then added to 308.4 g of fatty alcohol (hexadecanol: 70%, octadecanol: 30% by weight) containing 1.1 g of sulphuric acid, at a temperature of 90° C. over a period of 2 hours. The butanol is eliminated continuously under reduced pressure during the addition. Then, at the same time temperature, the acidity of the medium is neutralised with a 30.5% aqueous sodium hydroxide solution to pH 7 to 8 and the product is decolorised in the presence of oxygenated water. After cooling to 20° C. and grinding of the solid obtained, 420 g of the composition are obtained, containing 56% by weight, based on the total weight of the fatty alcohol composition.

EXAMPLE 6
Process for preparing a composition based on polyglycoside derived from wheat fibres according to the invention 100 g of syrup 3 in Example 5 are added dropwise over 1½ hours to 92.5 g of n-butanol containing 0.9 g of sulphuric acid and 6 g of water at a temperature of the order of 100 to 105° C. The water is eliminated during the reaction by azeotropic distillation of the mixture of water and butanol. Then the reaction mixture obtained is added to 214.9 g of oleic alcohol containing 0.7 g of sulphuric acid at a temperature of 90° C. over 2 hours. The butanol is eliminated continuously under reduced pressure during the addition. Then, at the same time temperature, the acidity of the medium is neutralised with a 30.5% aqueous sodium hydroxide solution to pH 7 to 8 and the product is decolorised in the presence of oxygenated water. After cooling to 20° C. and grinding of the solid obtained, 290 g of the composition are obtained, containing 55.5% by weight, based on the total weight of the fatty alcohol composition.

EXAMPLE 7
Process for preparing a composition based on polyglycoside derived from wheat fibres according to the invention 150 g of syrup 3 in Example 5 are added dropwise over 1½ hours to 138.7 g of n-butanol containing 1.3 g of sulphuric acid and 9 g of water at a temperature of the order of 100 to 105° C. The water is eliminated during the reaction by azeotropic distillation of the mixture of water and butanol. Then the reaction mixture obtained is added to 357.3 g of fatty alcohol (hexadecanol: 50%, octadecanol: 50% by weight) containing 1.1 g of sulphuric acid at a temperature of 90° C. over 2 hours . The butanol is eliminated continuously under reduced pressure during the addition. Then, at the same time temperature, the acidity of the medium is neutralised with a 30.5% aqueous sodium hydroxide solution to pH 7 to 8 and the product is decolorised in the presence of oxygenated water. After cooling to 20° C., 470 g of the composition are obtained, containing 60% by weight, based on the total weight of the fatty alcohol composition.

EXAMPLE 8
Process for preparing a composition based on polyglycoside derived from maize bran according to the invention 2 g of dried maize br an containing 92% dry matter and containing, in relation to the dry matter, 30% starch, 8.5% protein and 36% hemicellulose are brought into contact with 10 kg of 2% sulphuric acid solution. The reaction medium is homogenised in a stirred reactor then brought to a temperature of 140° C. for 30 minutes. After hydrolysis, the mixture is pressed in a MARREL laboratory press to separate the waste 1 from the liquor 1. A liquor and a waste containing 19.56% and 45%, respectively, of dry matter are recovered.

The liquor 1 is then demineralised by ion exchange on a strong cationic resin (A 200), a weak anionic resin (A368S) and finally on a strong cationic resin (A 200). The liquor 2 obtained is then concentrated to 73.3% dry matter by evaporating the water under reduced pressure at 50° C. The composition of the syrup 3 obtained is shown in the following Table:

|  | SYRUP 3 |
|---|---|
| Dry matter (%) | 73.3 |
| D-glucose/dry matter (%) | 54.6 |
| Other hexoses/dry matter (%) | 4.6 |
| D-xylose/dry matter (%) | 14.2 |
| L-arabinose/dry matter (%) | 9.4 |
| Oligosaccharides/dry matter (%) | 6.1 |
| Purity of reducing sugars/dry matter (%) | 88.9 |

150 g of this syrup 3 are then added dropwise over 1½ hours to 138.5 g of n-butanol containing 2.2 g of sulphuric acid and 9 g of water at a temperature of the order of 100 to 105° C. The water is eliminated in the course of the reaction by azeotropic distillation of the water/butanol mixture. The reaction mixture obtained is then added to 306.7 g of fatty alcohol (tetradecanol 10%, hexadecanol: 55%, octadecanol: 35% by weight) containing 1.1 g of sulphuric acid, at a temperature of 90° C. over a period of 2 hours. The butanol is eliminated continuously under reduced pressure during the addition. Then, at the same time temperature, the acidity of the medium is neutralised with a 30.5% aqueous sodium hydroxide solution to pH 7 to 8 and the product is decolorised in the presence of oxygenated water. After cooling to 20° C. and grinding of the solid obtained, 421 g of the composition are obtained, containing 56% by weight, based on the total weight of the fatty alcohol composition.

EXAMPLE 9
Process for preparing a composition based on polyglycoside derived from maize pomace according to the invention A suspension of maize pomace (2 kg of dry matter of maize pomace per 10 kg of suspension) is prepared in a sulphuric acid solution (10% $H_2SO_4$/DM of pomace). The reaction medium is homogenised in a stirred reactor, then brought to a temperature of 120° C. for 1 hour. After hydrolysis, the reaction medium is slaked to pH 4.3 using a milk of lime containing 18% dry matter and is pressed in a MARREL laboratory press to separate the waste 1 from the liquor 1.

The liquor 1 is then demineralised by ion exchange on a strong cationic resin (A 200), then by electrodialysis. The liquor 2 obtained is then concentrated to 77.1% dry matter by evaporating the water under reduced pressure at 50° C. The composition of the syrup 3 obtained is given in the following Table:

|  | SYRUP 3 |
|---|---|
| Dry matter (%) | 77.1 |
| D-glucose/dry matter (%) | 23.4 |
| Other hexoses/dry matter (%) | 4.9 |
| D-xylose/dry matter (%) | 28.5 |
| L-arabinose/dry matter (%) | 20.8 |
| Oligosaccharides/dry matter (%) | 7.1 |
| Purity of reducing sugars/dry matter (%) | 84.7 |

100 g of this syrup 3 are then added dropwise over 1 hour to 102.4 g of n-butanol containing 1.5 g of sulphuric acid and 6.6 g of water at a temperature of the order of 100 to 105° C. The water is eliminated in the course of the reaction by azeotropic distillation of the water/butanol mixture. The reaction mixture obtained is then added to 227.7 g of fatty alcohol (hexadecanol: 70%, octadecanol: 30% by weight) at a temperature of 80° C. over a period of 2 hours. The butanol is eliminated continuously under reduced pressure during the addition. Then, at the same time temperature, the acidity of the medium is neutralised with a 30.5% aqueous sodium hydroxide solution to pH 7 to 8 and the product is decolorised in the presence of oxygenated water. After cooling to 20° C. and grinding of the solid obtained, 305 g of the composition are obtained, containing 58% by weight, based on the total weight of the fatty alcohol composition.

EXAMPLE 10

Example of the use of the self-emulsifying composition in Example 9 for preparing a cream 2 g of the self-emulsifying composition in Example 9 are suspended in 48 g of water obtained by osmosis. The mixture is heated to 50° C. and then stirred (500 rpm) for 2 minutes. The emulsion thus formed is then cooled to ambient temperature. Its viscosity after 1 day of maturing is 10,300 cp (BROOKFIELD DV II—25° C—12 rpm—module 3).

EXAMPLE 11

Example of the use of the self-emulsifying composition in Example 9 for the preparation of a fluid lotion 1 g of the self-emulsifying composition of Example 9 is suspended in 49 g of water obtained by osmosis. The mixture is heated to 50° C. and then stirred (500 rpm) for 2 minutes. The emulsion thus formed is then cooled to ambient temperature. Its viscosity after 1 day of maturing is 3000 cp (BROOKFIELD DV II—25° C.—12 rpm—module 3).

EXAMPLE 12

Example of the use of the composition of Example 3 for preparing a cream 2 g of the composition based on polyglycosides of Example 3, 7.5 g of isostearyl isostearate and 40.5 g of water obtained by osmosis are heated simultaneously to a temperature of 70° C., then homogenised (1500 rpm) at the same temperature for 1 minute and finally cooled with gentle stirring (300 rpm) to a temperature of the order of 25° C. After 1 day of maturing, the viscosity of the emulsion thus formed is 9500 cp (BROOKFIELD DV II—25° C.—12 rpm—module 3).

EXAMPLE 13

Example of use of the composition of Example 3 for preparing a cream

The lipophilic phase (15 g of isostearyl isostearate) which contains 4 g of the polyglycoside-based composition of Example 3 and the hydrophilic phase (81 g of water obtained by osmosis) are heated separately to a temperature of 70° C. The lipophilic phase is stirred vigorously (1500 rpm) and over a period of 2 minutes the hydrophilic phase is added until there is phase inversion characterised by an abrupt change in viscosity. The addition can then take place more rapidly (1 minute). Finally, the emulsion is allowed to cool with gentle stirring (300 rpm) to a temperature of the order of 25° C.

After 1 day of maturing, the viscosity of the emulsion thus formed is 12,000 cp (BROOKFIELD DV II—25° C.—12 rpm—module 3).

EXAMPLE 14

Example of use of the composition of Example 3 for preparing a cream

The lipophilic phase (15 g of isostearyl isostearate) and the hydrophilic phase (81 g of water obtained by osmosis) which contains 4 g of the polyglycoside-based composition of Example 3 are heated separately to a temperature of 70° C. The hydrophilic phase is stirred (1500 rpm) and the lipophilic phase is progressively added thereto. The emulsion is then allowed to cool with gentle stirring (300 rpm) to a temperature of the order of 25° C.

After 1 day of maturing, the viscosity of the emulsion thus formed is 10,500 cp (BROOKFIELD DV II— 25° C.—12 rpm—module 3).

COMPARATIVE EXAMPLE 15

Creaming indices of the emulsions prepared from compositions based on polyglycosides and fatty alcohols Preparation of the emulsions Compositions:

3% by weight, based on the total weight of the emulsion, of compositions based on polyglycosides and fatty alcohols 10% by weight of sunflower oil, based on the total weight of the emulsion 0.5% by weight of preservative (Phenonip®) based on the total weight of the emulsion water obtained by osmosis, q.s. ad 100% by weight.

Method:

The ingredients are successively weighed in a shallow beaker and heated for 10 minutes to 75° C. The medium is stirred for 1 minute at 15,000 rpm in a polytron. Stirring is continued using a bar magnet (200 rpm) for 30 minutes until the emulsion has cooled. The emulsion is left to stand for 24 hours at 25° C. before being analysed.

The creaming index is defined as the percentage by volume of residual emulsion after a treatment of destabilisation by centrifuging. The centrifuging process (4080 g for 1 hour) are identical for all the tests.

After centrifuging, the creaming index is the ratio of volume of residual emulsion over the total volume of the initial emulsion multiplied by 100.

All the emulsions based on polyglycosides and fatty alcohols used contain 55% by weight of a mixture of hexadecanol and octadecanol (50/50; weight/weight), based on the total weight of the compositions. The polyglycosides are made up of polyhexosides (polyglucosides in the synthesis Example 1) and/or polypentosides (polyxylosides in synthesis Example 2 and/or polyarabinosides in synthesis Example 3). The results are summarised in the following Tables:

| MAKEUP OF THE COMPOSITION BASED ON POLYGLYCOSIDES | | |
|---|---|---|
| Polyglucosides of synthesis Example 1 (%/total polyglycosides) | Polyxylosides of synthesis Example 2 (%/total polyglycosides) | Creaming index |
| 100 | 0 | 19.5% |
| 90 | 10 | 18.7% |
| 80 | 20 | 31.3% |
| 75 | 25 | 100% |
| 70 | 30 | 100% |
| 60 | 40 | 100% |
| 50 | 50 | 98.5% |
| 35 | 65 | 99.5% |

-continued

MAKEUP OF THE COMPOSITION BASED ON POLYGLYCOSIDES

| Polyglucosides of synthesis Example 1 (%/total polyglycosides) | Polyarbinosides of synthesis Example 3 (%/total polyglycosides) | Creaming index |
|---|---|---|
| 100 | 0 | 19.5% |
| 90 | 10 | 24.1% |
| 80 | 20 | 25.2% |
| 70 | 30 | 97.5% |
| 60 | 40 | 97% |
| 50 | 50 | 97.5% |
| 35 | 65 | 95.6% |

MAKEUP OF THE COMPOSITION BASED ON POLYGLYCOSIDES

| Polyglucosides of synthesis Example 1 (%/polyglycosides) | Polypentosides | | Creaming index |
|---|---|---|---|
| | Polyxylosides of synthesis Example 2 (%/polyglycosides) | Polyarabinosides of synthesis Example 3 (%/polyglycoside) | |
| 100 | 0 | 0 | 19.5% |
| 90 | 6 | 4 | 23.0% |
| 80 | 12 | 8 | 23.6% |
| 75 | 15 | 10 | 24.2 |
| 70 | 18 | 12 | 97.3% |
| 60 | 24 | 16 | 98% |
| 50 | 30 | 20 | 97.7% |
| 35 | 39 | 26 | 98.1% |

The Tables given above demonstrate that the compositions based on polyglycosides containing 25 to 65% by weight, based on the total weight of polyglycosides, of polypentosides selected from among the polyarabinosides, the polyxylosides and mixtures thereof and 35 to 75% by weight of polyhexosides such as polyglucosides, produce emulsions having a creaming index of nearly 100%, i.e. they are stable on being centrifuged; this is not true of compositions containing only polyhexosides such as the polyglucosides in synthesis Example 1.

COMPARATIVE EXAMPLE 16

Viscosity of emulsions prepared from compositions based on polyglycosides and fatty alcohols The method used is the same as in the previous Example, except that in this case the viscosity of the emulsions prepared from compositions based on polyglycosides is being measured. The viscosities are measured at 25° C. using a BROOKFIELD DV II viscometer (12 rpm—module 3). The results are summarised in the following Tables:

MAKEUP OF THE COMPOSITION BASED ON POLYGLYCOSIDES

| Polyglucosides of synthesis Example 1 (%/polyglycosides) | Polyxylosides of synthesis Example 2 (%/polyglycosides) | Viscosity (cp) |
|---|---|---|
| 100 | 0 | 2985 |
| 90 | 10 | 2350 |
| 80 | 20 | 2936 |
| 75 | 25 | 3305 |
| 70 | 30 | 4198 |
| 60 | 40 | 5800 |
| 50 | 50 | 5300 |

According to the Table the viscosities reflect the values of the creaming indices of the above comparative example.

Overall, the viscosity of the emulsions increases with the increase in the percentage of polyxylosides in the emulsifying composition. As a high viscosity for an emulsion is a good indicator of its future stability, this finding shows that the compositions according to the invention based on polyglycosides made up of mixtures of polyhexosides and polypentosides can be used to form emulsions which are more stable than those comprising only polyglucosides without any need to add to thickeners.

COMPARATIVE EXAMPLE 17

Comparison of the creaming indices of emulsions prepared from the emulsifying compositions according to the invention and from EMULGADE® PL 68/50

This Example is carried out in the same way as in Example 15 above, except that the polyglucosides of synthesis Example 1 are replaced by polyglucosides marketed by HENKEL under the name EMULGADE® PL 68/50. The results are summarised in the following Tables:

MAKEUP OF THE COMPOSITION BASED ON POLYGLYCOSIDES

| Polyglucosides of EMULGADE ® PL 68/50 (%/polyglycosides) | Polyxylosides of synthesis Example 2 (%/polyglycosides) | Creaming index |
|---|---|---|
| 100 | 0 | 72.0% |
| 90 | 10 | 85.2% |
| 80 | 20 | 81.5% |
| 70 | 30 | 92% |
| 60 | 40 | 97.1% |
| 50 | 50 | 99.2% |
| 35 | 65 | 99.5% |

MAKEUP OF THE COMPOSITION BASED ON POLYGLYCOSIDES

| Polyglucosides EMULGADE ® PL 68/50 (%/polyglycosides) | Polyarbinosides of synthesis Example 3 (%/total polyglycosides) | Creaming index |
|---|---|---|
| 100 | 0 | 72.0% |
| 90 | 10 | 86.4% |
| 80 | 20 | 84.0% |
| 70 | 30 | 93.0% |
| 60 | 40 | 98.9% |
| 50 | 50 | 99.5% |
| 35 | 65 | 99.8% |

The above Tables demonstrate that the compositions based on polyglycosides containing mixtures of polyglucosides and polypentosides selected from the polyarabinosides and polyxylosides produce emulsions which have higher creaming indices than do emulsifying compositions containing exclusively polyglycosides such as the product EMULGADE® PL 68/50 sold by HENKEL.

COMPARATIVE EXAMPLE 18

Comparison of the viscosities of emulsions prepared from the compositions according to the invention and from EMULGADE® PL 68/50

This example is carried out in the same way as Example 16 above, except that the polyglucosides of synthesis Example 1 are replaced by polyglucosides marketed by HENKEL under the name EMULGADE® PL 68/50. The results are summarised in the following Tables:

| MAKEUP OF THE COMPOSITION BASED ON POLYGLYCOSIDES | | |
| --- | --- | --- |
| Polyglucosides of EMULGADE ® PL 68/50 (%/polyglycosides) | Polyxylosides of synthesis Example 2 (%/polyglycosides) | Viscosity (cp) |
| 100 | 0 | 1330 |
| 90 | 10 | 2840 |
| 80 | 20 | 2670 |
| 70 | 30 | 4000 |
| 60 | 40 | 6000 |
| 50 | 50 | 7200 |
| 35 | 65 | 7250 |

-continued

| MAKEUP OF THE COMPOSITION BASED ON POLYGLYCOSIDES | | |
| --- | --- | --- |
| Polyglucosides EMULGADE ® PL 68/50 (%/polyglycosides) | Polyarbinosides of synthesis Example 3 (%/polyglycosides) | Viscosity (cp) |
| 100 | 0 | 1330 |
| 90 | 10 | 1500 |
| 80 | 20 | 2230 |
| 70 | 30 | 3200 |
| 60 | 40 | 5100 |
| 50 | 50 | 6400 |
| 35 | 65 | 6520 |

The viscosity of the emulsions increases with the rise in the percentage of polyxylosides or polyarabinosides in the emulsifying composition EMULGADE® PL 68/50. As a high viscosity for an emulsion is an indicator of its future stability, this finding shows that the compositions according to the invention based on polyglycosides made up of mixtures of polyhexosides and polypentosides make it possible to form emulsions which are more stable than those consisting solely of polyglucosides as is the case with EMULGADE® PL 68/50.

EXAMPLE 19

Stability of emulsions as a function of the concentration of oil and concentration of the polyglycoside-based composition according to the invention Preparation of the emulsions Compositions:
2.5 to 5% by weight, based on the total weight of the emulsion, of compositions based on polyglycosides and fatty alcohols of Example 3, 5 and 7
0 to 80% by weight, based on the total weight of the emulsion, of sunflower oil
0.5% by weight, based on the total weight of emulsion, of preservative (Phenonip® consisting of mixtures of methyl/ethyl/butyl/propyl parabenes and phenoxyethanol marketed by NIPA)
water obtained by osmosis q.s. ad 100% by weight.

Method:
The ingredients are successively weighed and heated to 75° C. for 10 minutes. The medium is stirred for 1 minute at 15,000 rpm using a polytron. Stirring is continued with a bar magnet (200 rpm) for 30 minutes until the emulsion has cooled. The emulsion is left to mature in a dryer at 45° C. An emulsion is regarded as stable when there is no change in phase after 90 days at 45° C.

| Nature and quantity of composition | | Quantity of fatty phase (sunflower oil) | | | | | | | | |
| --- | --- | --- | --- | --- | --- | --- | --- | --- | --- | --- |
| | | 0% | 10% | 20% | 30% | 40% | 50% | 60% | 70% | 80% |
| Composition of Example 5 | 5% | + | + | + | + | + | + | + | + | − |
| | 4% | + | + | + | + | + | + | + | − | − |
| | 3% | + | + | − | − | − | − | + | − | − |
| Composition of Example 7 | 5% | + | + | + | + | + | + | + | − | − |
| | 4% | + | + | − | − | + | + | + | − | − |
| | 2.5% | + | − | − | − | − | − | − | − | + |
| Composition of Example 3 | 5% | + | + | + | + | + | + | + | + | − |
| | 4% | + | + | + | + | + | + | + | + | − |
| | 3% | + | + | + | − | − | − | nd | nd | nd |

Legend relating to Table:
+: stable emulsion
−: unstable emulsion
nd: not determined Being endowed with a strong emulsifying power, the compositions based on polyglycosides according to the invention can be used to obtain emulsions which are stable even when they are incorporated in small amounts (less than 5% by weight based on the total weight of the emulsion), even in the presence of sunflower oil which is known to be difficult to emulsify.

EXAMPLE 20

Stability of emulsions as a function of the nature and concentration of the fatty phase Preparation of emulsions Compositions:
5% by weight, based on the total weight of emulsion, of compositions based on polyglycosides and fatty alcohols of Examples 3, 5 and 7.
0 to 80% by weight, based on the total weight of the emulsion, of oily phase
0.5% by weight, based on the total weight of the emulsion, of preservative (Phenonip®)
water obtained by osmosis q.s. ad 100% by weight.

The oily phases used are as follows:
sunflower oil
liquid paraffin oil MARCOL 82 (ESSO)
capric/caprilic triglyceride MIGLYOL 812N (HULS)

Method:

The ingredients are successively weighed and heated to 75° C. for 10 minutes. The medium is stirred for 1 minute at 15,000 rpm using a polytron. Stirring is continued with a bar magnet (200 rpm) for 30 minutes until the emulsion has cooled. The emulsion is left to mature in a dryer at 45° C. An emulsion is regarded as stable when there is no change in phase after 90 days at 45° C.

| Compositions | Oily phases | Quantities of oily phase | | | | | | | | |
|---|---|---|---|---|---|---|---|---|---|---|
| | | 0% | 10% | 20% | 30% | 40% | 50% | 60% | 70% | 80% |
| Composition of Example 5 | sunflower | + | + | + | + | + | + | + | + | − |
| | paraffin | + | + | + | + | + | + | + | + | − |
| | Miglyol | + | + | + | + | + | + | + | + | − |
| Composition of Example 7 | sunflower | + | + | + | + | + | + | + | + | − |
| | paraffin | + | + | + | + | + | + | + | + | − |
| | Miglyol | + | + | + | + | + | + | + | + | − |
| Composition of Example 3 | sunflower | + | + | + | + | + | + | + | − | − |
| | paraffin | + | + | + | + | + | + | + | − | − |
| | Miglyol | + | + | + | + | + | + | + | + | − |

Legend relating to the Table:
+: stable emulsion
−: unstable emulsion

With all the oils tested, the compositions of the invention produce emulsions which are highly stable over a large range of oily phase contents (0 to 70% based on the total weight of the emulsion).

0.5% by weight, based on the total weight of the emulsion, of preservative (Phenonip®)

water obtained by osmosis, q.s. ad 100% by weight.

Method:

The ingredients are successively weighed and heated to 75° C. for 10 minutes. The medium is stirred for 1 minute at 15,000 rpm using a polytron. Stirring is continued with a bar magnet (200 rpm) for 30 minutes until the emulsion has cooled. The emulsion is left to mature in a dryer at 45° C. An emulsion is regarded as stable when there is no change in phase after 90 days at 45° C.

| Nature and content of compositions | | Quantities of oily phase | | | | | | | |
|---|---|---|---|---|---|---|---|---|---|
| | | 0% | 10% | 20% | 30% | 40% | 50% | 60% | 70% |
| Composition of Example 5 | 5% | L | L | C | C | C | P | P | P |
| | 4% | L | L | C | C | C | P | P | P |
| | 3% | L | L | − | − | − | − | P | − |
| Composition of Example 7 | 5% | C | C | C | C | C | C | P | − |
| | 4% | C | C | − | − | C | C | C | − |
| | 2.5% | C | − | − | − | − | − | − | − |
| Composition of Example 3 | 5% | L | C | C | P | P | P | P | P |
| | 4% | L | C | C | C | P | P | P | P |
| | 3% | L | L | L | − | − | − | nd | nd |

Legend relating to the Table:
L: lotion
C: cream
P: ointment
−: unstable emulsion
nd: not determined

EXAMPLE 21

Influence of the content of fatty phase on the appearance of the emulsions

Preparation of emulsions

Compositions:

2.5 to 5% by weight, based on the total weight of emulsion, of compositions based on polyglycosides and fatty alcohols in Examples 3, 5 and 7.

0 to 70% by weight, based on the total weight of the emulsion, of oily phase (sunflower oil)

As for the appearance of the emulsions, we find that the compositions according to the invention produce perfectly stable emulsions without the addition of specific thickeners or additives, and this applies to lotions, creams and ointments.

EXAMPLE 22

Comparative Example

Stability of Emulsions as a Function of the Quantity of Fatty Phase and the Content of Emulsifying Composition Preparation of emulsions Compositions:

2.5 to 5% by weight, based on the total weight of emulsion, of compositions based on polyglycosides and fatty alcohols in Examples 3, 5 and 7 or other commercially available compositions.
0 to 80% by weight, based on the total weight of the emulsion, of oily phase (sunflower oil)
0.5% by weight, based on the total weight of the emulsion, of preservative (Phenonip®)
water obtained by osmosis, q.s. ad 100% by weight.

The commercially available compositions are as follows:
Composition based on alkyl polyosides and fatty alcohol: MONTANOV® 68 (SEPPIC)
PEG palmitostearate SE TEFOSE® 1500 (GATTEFOSSE)
Beeswax SE APIFIL® (GATTEFOSSE)
Glyceryl stearate SE CUTINA® (HENKEL)
Composition based on polyoxyethylenated surfactants and fatty alcohols: SINNOWAX AOE (HENKEL)

Method:
The ingredients are successively weighed and heated to 75° C. for 10 minutes. The medium is stirred for 1 minute at 15,000 rpm using a polytron. Stirring is continued with a bar magnet (200 rpm) for 30 minutes until the emulsion has cooled. The emulsion is left to mature in a dryer at 45° C. An emulsion is regarded as stable when there is no change in phase after 90 days at 45° C.

Preparation of the emulsions

Compositions:

2.5 to 5% by weight, based on the total weight of emulsion, of compositions based on polyglycosides and fatty alcohols containing different amounts of fatty alcohol.
0 to 80% by weight, based on the total weight of the emulsion, of oily phase (sunflower oil)
0.5% by weight, based on the total weight of the emulsion, of preservative (Phenonip®)
water obtained by osmosis, q.s. ad 100% by weight.

Compositions used:

A—Composition of Example 7 containing 60% by weight of cetaryl alcohol (hexadecanol/octadecanol 50/50) based on the total weight of the composition.

B—Composition of Example 7 wherein cetaryl alcohol (hexadecanol/octadecanol 50/50) has been added so that it contains 75% by weight of cetaryl alcohol compared with the total weight of the composition.

| Nature and content of emulsifying composition | | Quantity of fatty phase | | | | | | | | |
|---|---|---|---|---|---|---|---|---|---|---|
| | | 0% | 10% | 20% | 30% | 40% | 50% | 60% | 70% | 80% |
| Composition of Example 5 | 5% | + | + | + | + | + | + | + | + | − |
| | 4% | + | + | + | + | + | + | + | + | − |
| | 3% | + | + | − | − | − | − | + | − | − |
| Composition of Example 7 | 5% | + | + | + | + | + | + | + | − | − |
| | 4% | + | + | − | − | + | | + | − | − |
| | 2.5% | + | − | − | − | − | − | − | − | + |
| Composition of Example 3 | 5% | + | + | + | + | + | + | + | + | − |
| | 4% | + | + | + | + | + | + | + | + | − |
| | 3% | + | + | + | − | − | − | nd | nd | nd |
| Montanov ® 68 | 5% | − | + | + | + | + | + | − | − | − |
| | 4% | − | − | − | − | − | − | − | − | − |
| | 3% | + | − | − | − | − | − | − | − | − |
| TEFOSE ® 1500 | 5% | − | − | − | − | − | − | − | − | − |
| | 4% | − | − | − | − | − | − | − | − | − |
| | 3% | + | − | − | − | − | − | − | − | − |
| APIFIL® | 5% | − | − | − | − | − | − | − | − | − |
| | 4% | + | − | − | − | − | − | − | − | − |
| | 3% | + | − | − | − | − | − | − | − | − |
| CUTINA® | 5% | + | − | + | + | + | + | − | − | − |
| Sinnovax® AOE | 5% | + | + | + | + | − | − | − | − | − |
| | 4% | − | − | − | − | − | − | − | − | − |
| | 3% | − | − | − | − | − | − | − | − | − |

Legend relating to the Table:
+: stable emulsion
−: unstable emulsion
nd: not determined The above Table shows that the compositions according to the invention have ranges of stability for the emulsions which are far wider than those obtained with rival compositions. Compared with the composition MONTANOV® 68 consisting of polyglucosides and cetaryl alcohol, the compositions according to the invention made up of mixtures of polyhexosides and polypentosides have a wider range of stability particularly at low concentrations in an emulsifying agent.

EXAMPLE 23

Influence of the content of fatty alcohols in the compositions according to the invention on the stability of emulsions prepared from these compositions C—Composition of Example 7 wherein cetaryl alcohol (hexadecanol/octadecanol 50/50) has been added so that it contains 90% by weight of cetaryl alcohol based on the total weight of the composition.

Method:

The ingredients are successively weighed and heated to 75° C. for 10 minutes. The medium is stirred for 1 minute at 15,000 rpm using a polytron. Stirring is continued with a bar magnet (200 rpm) for 30 minutes until the emulsion has cooled. The emulsion is left to mature in a dryer at 45° C. An emulsion is regarded as stable when there is no change in phase after 90 days at 45° C.

| Nature and content of emulsifying composition | | Sunflower oil | | | | | | | | |
|---|---|---|---|---|---|---|---|---|---|---|
| | | 0% | 10% | 20% | 30% | 40% | 50% | 60% | 70% | 80% |
| Composition A | 5% | + | + | + | + | + | + | + | – | – |
| | 4% | + | + | – | – | + | + | + | – | – |
| 60% alcohol | 2.5% | + | – | – | – | – | – | – | – | + |
| Composition B | 5% | + | + | + | – | + | + | + | – | – |
| | 4% | + | + | – | – | – | – | – | – | – |
| 75% alcohol | 2.5% | + | – | – | – | – | – | – | + | + |
| Composition C | 5% | + | – | – | – | – | + | + | – | – |
| | 4% | + | + | – | – | – | – | – | – | – |
| 90% alcohol | 2.5% | – | – | – | – | – | – | – | – | – |

Legend relating to the Table:
+: stable emulsion
–: unstable emulsion

The above Table shows that when the content of fatty alcohol increases in the compositions the latter becomes less effective and the ranges of stability of the emulsions formed are more restricted. This is why compositions based on polyglycosides and fatty alcohols according to the present invention contain at most 65% by weight of free fatty alcohols, based on the total weight of the compositions.

EXAMPLE 24

Comparative Example

Viscosity of Emulsions as a Function of the Sodium Chloride Content

The emulsions in this Example are prepared as follows:

The fatty phase and aqueous phase are heated separately for 10 minutes to 75° C. The fatty phase contains 4% by weight, based on the total weight of the emulsion, of emulsifying composition according to Example 1 or of the composition EMULGADE® PL 68/50, 10% of isostearyl isostearate and 0.5% of preservative (Phenonip®).

The aqueous phase contains 0 to 2%, based on the total weight of the emulsifying composition, of sodium chloride and water (q.s. ad 100% by weight based on the total weight of the emulsion).

The aqueous phase is added to the oily phase at 750C with stirring (1300 rpm) and stirring is continued at this speed for 5 minutes.

Stirring is continued using a bar magnet 260 rpm for 15 minutes until the emulsion has cooled. The emulsion is left to stand at 25° C. for 8 days and its viscosity is measured using a BROOKFIELD viscometer DV II, module 3, 12 rpm at 25° C.

The results are summarised in the following Table:

| Content of NaCl | Viscosity of emulsion prepared from composition of Example 1 | Viscosity of emulsion prepared from composition EMULGADE® PL 68/50 |
|---|---|---|
| 0% | 30000 cp | 32000 cp |
| 0.25% | 26000 cp | 22000 cp |
| 0.5% | 29000 cp | 17000 cp |
| 0.75% | 34000 cp | 16000 cp |
| 1% | 33000 cp | 17500 cp |
| 2% | 35000 cp | 14000 cp |

The comparative Table shown above demonstrates that the composition based on polyglycosides according to Example 1 of the present invention has low sensitivity to sodium chloride compared with the composition EMULGADE® PL 68/50. Thus, the viscosity of the emulsions formed is more of less constant regardless of the quantity of sodium chloride.

EXAMPLE 25

Water-resistant self-tanning and moisturising cream

| | | |
|---|---|---|
| A | Composition of Example 8 | 4.0% |
| | Aloe vera | 1.0% |
| | Shea tree butter | 0.2% |
| | Dimethicone | 2.0% |
| | 2-octyl dodecyl myristate (MCD) | 3.0% |
| | Propylglycol stearate (Stepan PGMS) | 1.0% |
| | Stearic acid | 1.0% |
| | Vitamin E | 0.1% |
| | Hyaluronic acid (VITALHYAL) | 1.0% |
| | Phenonip | 0.5% |
| | Water q.s. ad | 100% |
| B | Carbopol Ultrez 10 (BF Goodrich) | 0.15% |
| | Water | 14.85% |
| C | Hydroxyace acetone | 5.0% |
| | Water | 10.0% |
| D | Fragrance | q.s. |

Method of producing the cream:
  All the ingredients of A are weighed
  All the ingredients of B are weighed and a dispersion is formed
  B is added to A
  The mixture is heated to 75° C.
  It is mixed at 2000 rpm at 75° C. for a few minutes
  It is left to cool to 30° C. whilst stirring at 300 rpm
  Solution C is prepared at ambient temperature
  C and D are added to the emulsion
  The pH is corrected if necessary.

EXAMPLE 26

Moisturising Lotion

| | |
|---|---|
| Composition of Example 5 | 2.0% |
| Miglyol 812 N | 3.0% |
| Isostearyl isostearate | 3.0% |
| Dimethicone | 2.0% |
| Stearyl alcohol | 1.0% |
| Hyaluronic acid (VITALHYAL) | 1.0% |
| Phenonip | 0.5% |
| Water q.s. ad | 100% |

Process for producing the lotion:
All the ingredients are weighed
They are heated to 75° C.
They are mixed at 3000 rpm for some minutes at 75° C.
The mixture is cooled to 30° C. while stirring at 500 rpm
The pH is corrected if necessary.

EXAMPLE 27

Night Cream

| | |
|---|---|
| Composition of Example 9 | 4.0% |
| Diisopropyl adipate | 5.0% |
| Oleyl erucate (Cetiol J600) | 1.5% |
| Jojoba oil | 1.5% |
| Camelia oil | 1.5% |
| Sweet almond oil | 0.5% |
| Hexanol (SIPOL 916) | 2.0% |
| Hyaluronic acid (VITALHYAL) | 2.0% |
| Wheat protein hydrolysate | 0.5% |
| Vitamin E | 0.1% |
| Phenonip | 0.5% |
| Perfume | q.s. |
| Water q.s. ad | 100% |

Process for producing the cream:
All the ingredients are weighed except for the perfume
They are heated to 75° C.
They are mixed at 3000 rpm at 75° C. for a few minutes
The mixture is cooled to 30° C. with stirring at 300 rpm
The perfume is added
Stirring is stopped
The pH is corrected if necessary.

EXAMPLE 28

Cream

| | |
|---|---|
| Composition of Example 5 | 4.0% |
| Sweet almond oil | 2.0% |
| Miglyol 812 N | 2.0% |
| Isostearyl isostearate | 2.0% |
| Paraffin oil (MARCOL 82) | 2.0% |
| Dimethicone | 2.0% |
| Octadecanol (steraffin) | 1.0% |
| Vitamin E | 0.2% |
| Phenonip | 0.5% |
| Perfume | q.s. |
| Water q.s. ad | 100% |

Process for producing the cream:
All the ingredients are weighed except for the perfume
They are heated to 75° C.
They are mixed at 3000 rpm at 75° C. for a few minutes
The mixture is cooled to 30° C. with stirring at 300 rpm
The perfume is added
Stirring is stopped
The pH is corrected if necessary.

EXAMPLE 29

Makeup Removing Lotion

| | |
|---|---|
| Composition of Example 2 | 2.0% |
| Sweet almond oil | 2.0% |
| Miglyal 812 N | 2.0% |
| Isostearyl isostearate | 2.0% |
| Propylglycol stearate (Stepan PGMS) | 1.0% |
| Dimethicone | 2.0% |
| Hexanol (SIPOL C16) | 1.0% |
| Lipid sophoroses (SOPHOLIANCE) | 2.0% |
| Wheat protein hydrolysate | 0.2% |
| Vitamin E | 0.2% |
| Phenonip | 0.5% |
| Perfume | q.s. |
| Water q.s. ad | 100% |

Process for producing the lotion:
All the ingredients are weighed except for the perfume
They are heated to 75° C.
They are mixed at 3000 rpm at 750° C. for a few minutes
The mixture is cooled to 30° C. with stirring at 300 rpm
The perfume is added
Stirring is stopped
The pH is corrected if necessary.

EXAMPLE 30

Sun Cream

| | | |
|---|---|---|
| A. | Composition of Example 5 | 3.0% |
| | Sunflower oil | 2% |
| | Miglyol 812 N | 1% |
| | Paraffin oil | 3% |
| | Phenonip | 0.5% |
| | Vitamin E | 0.1% |
| | Water q.s. | 100% |
| B. | Titanium dioxide | 3.0% |
| | Dimethicone | 5.0% |
| C. | DHA | 5.0% |
| | Water | 10.0% |

Process
the ingredients of A are weighed
they are heated to 50° C.
B is intimately mixed
A is stirred at 2000 rpm and at 50° C. for a few minutes
B is added while stirring is continued for some minutes
stirring is slowed down to 2/300 rpm and to 30/35° C.
C is added when the temperature is below 40° C.
the pH is corrected (to between 4 and 6)

EXAMPLE 31

Cream Containing Lipid Sophoroses

| | |
|---|---|
| Composition of Example 5 | 4.0% |
| Paraffin oil (MARCOL 82) | 2.0% |
| Miglyol 812 N | 3.0% |
| Isostearyl isostearate | 3.0% |
| Dimethicone | 2.0% |
| Octadecanol (steraffin) | 2.0% |
| Lipid sophoroses (SOPHOLIANCE) | 1.0% |
| Phenonip | 0.5% |
| Water q.s. ad | 100% |

Process for producing the cream:
- A clear aqueous solution of SOPHOLIANCE is prepared containing 25% dry matter at pH 6 (NaOH)
- All the ingredients except SOPHOLIANCE are weighed
- They are heated to 75° C. for 10 minutes
- They are mixed at 1500 rpm and at 75° C. for 1 minute
- They are cooled with stirring at 300 rpm
- SOPHOLIANCE is added towards 50° C.
- The pH is corrected if necessary
- Stirring is stopped at around 30° C.

EXAMPLE 32

Moisturising Cream for the Hands

* Special feature

Moisturing O/W cream, non-sticky, giving a feeling of freshness to the hands and having a texture which is suitable for use with greasy skins.

* Formulation

| Excipients | Percentages |
|---|---|
| 1 - Arlamol S7 (silicone) | 11% |
| 2 - Composition of Example 5 | 4% |
| 3 - Composition of Example 4 | 1% |
| 4 - Glycerol | 4% |
| 5 - Preservative - (Phehonip) | 0.5% |
| 6 - Antioxidant | 0.1% |
| 7 - Water q.s. ad | 100% |

* Procedure

Excipients 1, 2, 3, 4, 5 and 7 are heated to 70° C. with stirring,
6 is added at ambient temperature.

EXAMPLE 33

Moisturising Cream for Babies and Dry Skins

* Special feature

Moisturising O/W cream which is non-sticky and easy to apply for babies and dry skins.

* Formulation

| Excipients | Percentages |
|---|---|
| 1 - Vaseline | 7.5 |
| 2 - Composition of Example 5 | 5 |
| 3 - Miglyol 812 N | 3.5 |
| 4 - Isopropyl myristate | 2 |
| 5 - Calendula oil | 1 |

-continued

| Excipients | Percentages |
|---|---|
| 6 - Avocado oil | 1 |
| 7 - Phenonip | 0.5 |
| 8 - Antioxidant | 0.1 |
| 9 - Water q.s. ad | 100 |

* Procedure

Excipients 1 to 7 and 9 are heated to 70° C., with stirring and 8 is added at ambient temperature.

EXAMPLE 34

Moisturising Lotion Rich in Plant Oils

* Special feature

Highly moisturising O/W lotion, non-sticky, rich in plant oils and easy to apply.

* Formulation

| Excipients | Percentages |
|---|---|
| 1 - Miglyol 812 N | 3 |
| 2 - Isopropyl myristate | 3 |
| 3 - Composition of Example 5 | 3 |
| 4 - Hazelnut oil | 2 |
| 5 - Apricot oil | 2 |
| 6 - Thickener (Methocel 40-202-E) | 1 |
| 7 - Preservative (Phenonip) | 0.5 |
| 8 - Antioxidant | 0.1 |
| 9 - Water q.s. ad | 100 |

* Procedure

All the excipients except 8 are heated to 70° C. with stirring,
Then 8 is added at ambient temperature.

EXAMPLE 35

Sun Lotion

* Special feature

O/W sun lotion, non-sticky and photostable, anti-IR, $UV_A$, $UV_B$ and $UV_C$.

* Formulation

| Excipients | Percentages |
|---|---|
| 1 - $UV_A$, $UV_B$ and $UV_C$ filter (Covabsorb) | 8 |
| 2 - Miglyol 812 N | 3 |
| 3 - Isopropyl myristate | 3 |
| 4 - Composition of Example 5 | 2 |
| 5 - Composition of Example 6 | 1 |
| 6 - Hazelnut oil | 2 |
| 7 - Apricot oil | 2 |
| 8 - IR filter (titanium dioxide) | 2 |
| 9 - Thickener (Methocel 40-202-E) | 1 |
| 10 - Preservative (Phenonip) | 0.6 |
| 11 - Water q.s. ad | 100 |

* Procedure

All the excipients are heated to 70° C., with stirring, and the pH is adjusted if necessary.

What is claimed is:

1. A composition of polyglycosides which comprises 30 to 65% by weight of at least one fatty alcohol of formula ROH, where R is a straight-chained or branched aliphatic radical which is saturated or unsaturated having 0 to 4 ethylenically unsaturated bonds and having 12 to 22 carbon atoms, the remainder being, apart from impurities, selected from the group consisting (a) a mixture of polyglycosides containing 35 to 75% by weight of at least one polyhexoside of formula:

$$R^1O(H_x)_{n1}$$

wherein $R^1$ is a straight-chained or branched aliphatic radical which is saturated or unsaturated having 0 to 4 ethylenically unsaturated bonds and with 12 to 22 carbon atoms, and $H_x$ is a radical of a hexose, n1 is between 1 and 5; and 25 to 65% by weight of at least one polypentoside of formula:

$$R^2O(P_n)_{n2}$$

wherein $R^2$ is a straight-chained or branched aliphatic radical which is saturated or unsaturated having 0 to 4 ethylenically unsaturated bonds, and having 12 to 22 carbon atoms, and $P_n$ is a radical of a pentose selected from the group consisting of arabinose and xylose, n2 is between 1 and 5;

(b) a mixture of polyglycosides of formula:

$$R^3(G_1)_a(G_2)_b(G_3)_c(G_4)_d(G_5)_e$$

wherein $R^3$ is a straight-chained or branched aliphatic radical which is saturated or unsaturated having 0 to 4 ethylenically unsaturated bonds and having 12 to 22 carbon atoms, $G_1$, $G_2$, $G_3$, $G_4$ and $G_5$ independently of one another are residues of an ose selected from the group consisting of hexoses and pentoses, the latter being selected from the group consisting of arabinose and xylose, the hexoses representing 35 to 75% by weight of all the residues of oses $G_1$, $G_2$, $G_3$, $G_4$ and $G_5$ and the pentoses representing 25 to 75% by weight of all the residues of oses $G_1$, $G_2$, $G_3$, $G_4$ and $G_5$; a, b, c, d and e being equal to 0 or 1, and the sum of a, b, c, d and e being at least 1; and (c) a mixture of (a) and (b).

2. The composition according to claim 1, wherein the polyhexosides or hexose residues are made up, respectively, of at least 80% of polyglucosides or glucose residues.

3. The composition according to claim 1 which comprises polyglycosides wherein the $R^1$ and $R^2$ radicals or the radical $R^3$ are identical to the radical R of the fatty alcohol.

4. The composition according to claim 1, wherein the fatty alcohol comprises 14 to 22 carbon atoms.

5. The composition according to claim 4, wherein the fatty alcohol is a mixture of alcohols having 16 to 18 carbon atoms.

6. The composition according to claim 1 which comprises 40 to 60% of fatty alcohol.

7. The composition according to claim 1 which comprises a mixture of 45 to 70% by weight, based on the polyglycosides, of polyhexosides of formula $R^1O(H_x)_{n1}$ and 30 to 55% by weight of polypentosides of formula $R^2O(P_n)_{n2}$.

8. The composition according to claim 1 which comprises polyglycosides of formula:

$$R^3O(G_1)_a(G_2)_b(G_3)_c(G_4)_d(G_5)_e$$

wherein the hexose residues represent 45 to 70% by weight of all the ose residues $G_1$, $G_2$, $G_3$, $G_4$ and $G_5$ and the pentose residues constitute 30 to 55% by weight of all the ose residues $G_1$, $G_2$, $G_3$, $G_4$ and $G_5$.

9. The composition according to claim 1, wherein the polyglycosides are derived from sugar syrups obtained by hydrolysing by-products of vegetable origin rich in starch and hemicellulose.

10. The composition according to claim 1, wherein the polyglycosides are derived from plant materials selected from the group consisting of wheat bran, mixtures of starch and wheat bran, maize bran, maize pomace and mixtures thereof.

11. The composition according to claim 1 which comprises 52 to 57% of fatty alcohol.

12. A process for preparing an emulsion comprising contacting:

a) 2 to 60% by weight of an oily phase;
b) 1 to 10% by weight of a composition based on polyglycosides which comprises 30 to 65% by weight of at least one fatty alcohol of formula ROH, where R is a straight-chained or branched aliphatic radical which is saturated or unsaturated having 0 to 4 ethylenically unsaturated bonds and having 12 to 22 carbon atoms, the remainder being, apart from impurities, selected from the group consisting of:

(1) a mixture of polyglycosides containing 35 to 75% by weight of at least one polyhexoside of formula:

$$R^1O(H_x)_{n1}$$

wherein $R^1$ is a straight-chained or branched aliphatic radical which is saturated or unsaturated having 0 to 4 ethylenically unsaturated bonds and with 12 to 22 carbon atoms, and $H_x$ is a radical of a hexose, n1 is between 1 and 5; and 25 to 65% by weight of at least one polypentoside of formula:

$$R^2O(P_n)_{n2}$$

wherein $R^2$ is a straight-chained or branched aliphatic radical which is saturated or unsaturated having 0 to 4 ethylenically unsaturated bonds, and having 12 to 22 carbon atoms, $P_n$ is a radical of a pentose selected from the group consisting of arabinose and xylose, n2 is between 1 and 5;

(2) a mixture of polyglycosides of formula:

$$R^3O(G_1)_a(G_2)_b(G_3)_c(G_4)_d(G_5)_e$$

wherein $R^3$ is a straight-chained or branched aliphatic radical which is saturated or unsaturated having 0 to 4 ethylenically unsaturated bonds and having 12 to 22 carbon atoms, $G_1$, $G_2$, $G_3$, $G_4$ and $G_5$ independently of one another are residues of an ose selected from the hexoses and pentoses, the latter being selected from the group consisting of arabinose and xylose, the hexoses representing 35 to 75% by weight of all the residues of oses $G_1$, $G_2$, $G_3$, $G_4$ and $G_5$ and the pentoses representing 25 to 75% by weight of all the residues of oses $G_1$, $G_2$, $G_3$, $G_4$ and $G_5$; a, b, c, d and e being equal to 0 or 1, and the sum of a, b, c, d and e being at least 1; and (3) a mixture of (1) and (2); and c) the remainder of the emulsion selected from the group consisting of an aqueous phase and an aqueous phase to which has been added an emulsifying composition other than the one specified in b).

13. The process according to claim 12, wherein the oily phase of the emulsion contains at least 50% by weight, based on the total weight of the oily phase, of plant oils containing at least 40% of compounds selected from the group consisting of the linolenic acid triglycerides and the silicon oils.

14. The process according to claim 13, wherein composition b) represents 3 to 4% by weight of the total weight of the emulsion.

15. The process according to claim 12, wherein the oily phase represents 10 to 40% by weight based on the total weight of the emulsion.

* * * * *

UNITED STATES PATENT AND TRADEMARK OFFICE
CERTIFICATE OF CORRECTION

PATENT NO.   : 6,087,403
DATED        : July 11, 2000
INVENTOR(S)  : Jean-Noel Bertho et al.

It is certified that error appears in the above-identified patent and that said Letters Patent is hereby corrected as shown below:

Column 30,
Line 67, change "consisting" to -- consisting of: --.

Signed and Sealed this

Twenty-fifth Day of February, 2003

JAMES E. ROGAN
*Director of the United States Patent and Trademark Office*